United States Patent [19]

Herrington

[11] 4,015,126
[45] Mar. 29, 1977

[54] X-RAY INTENSIFICATION AND MINIFICATION SYSTEM

[75] Inventor: James R. Herrington, Garland, Tex.
[73] Assignee: Varo Semiconductor, Inc., Garland, Tex.
[22] Filed: Oct. 10, 1975
[21] Appl. No.: 621,405
[52] U.S. Cl. .................... 250/320; 250/213 VT; 250/369; 250/475; 250/483
[51] Int. Cl.² .................................... G03B 5/17
[58] Field of Search .......... 250/320, 321, 323, 361, 250/362, 367, 369, 475, 476, 477, 483, 213 VT; 354/62, 105, 151

[56] References Cited

UNITED STATES PATENTS

| | | | |
|---|---|---|---|
| 2,595,430 | 5/1952 | Tuttle et al. | 250/477 |
| 3,126,480 | 3/1964 | Bouwers | 250/322 |
| 3,417,242 | 12/1968 | Windebank | 250/367 |
| 3,770,963 | 11/1973 | Vandervelden et al. | 250/409 |
| 3,797,025 | 3/1974 | Murphy, Jr. et al. | 354/105 X |
| 3,827,070 | 7/1974 | Hoerenz et al. | 250/476 UX |

Primary Examiner—Davis L. Willis
Attorney, Agent, or Firm—Richards, Harris & Medlock

[57] ABSTRACT

The specification discloses apparatus for intensifying and minifying X-ray images which includes a rectangular housing having opposed front and rear ends. A phosphorous screen is disposed in the front end of the housing for receiving X-ray images of an object irradiated by X-rays and in response thereto generating light images corresponding to the X-ray images. A mirror system is mounted within the housing adjacent the rear end for reflecting the light images back toward the front end of the housing. An image intensifying assembly is provided along one side of the housing for amplifying and minifying the reflected light images. A camera is located in the front end of the housing for recording the amplified and minified light images. Circuitry is provided for interrogating the operation of the camera and of various electronic circuits of the system in order to provide a visual indication of malfunction of the system.

39 Claims, 13 Drawing Figures

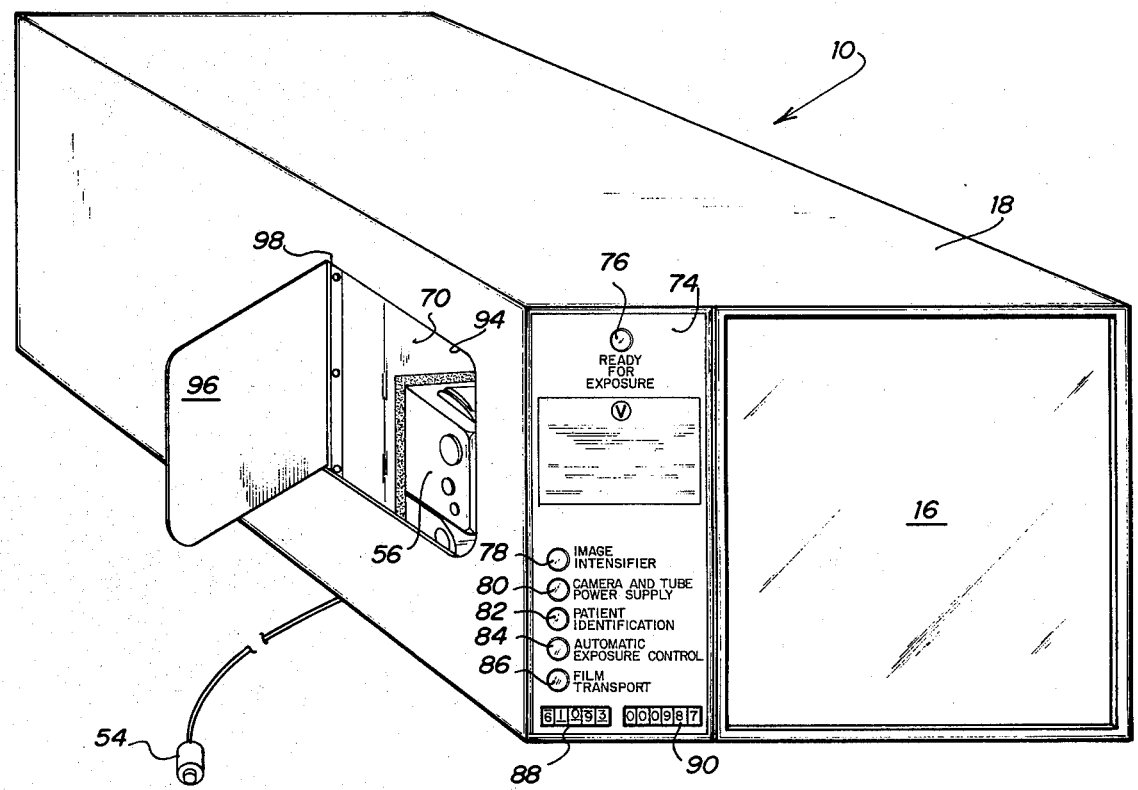
FIG. 2
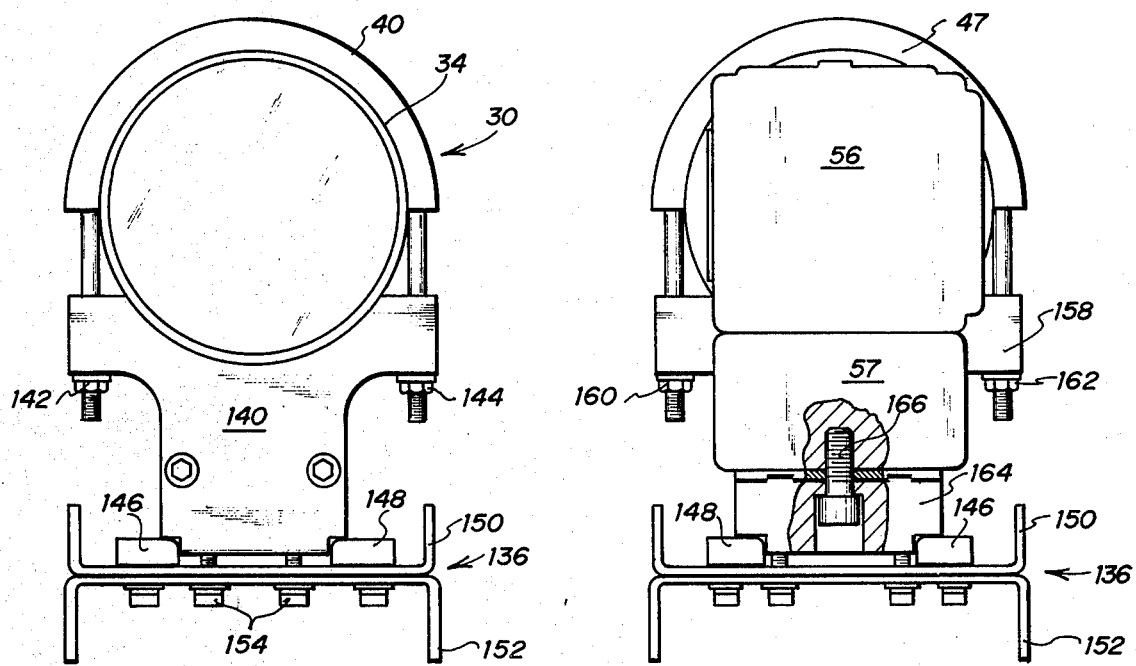
FIG. 5
FIG. 6

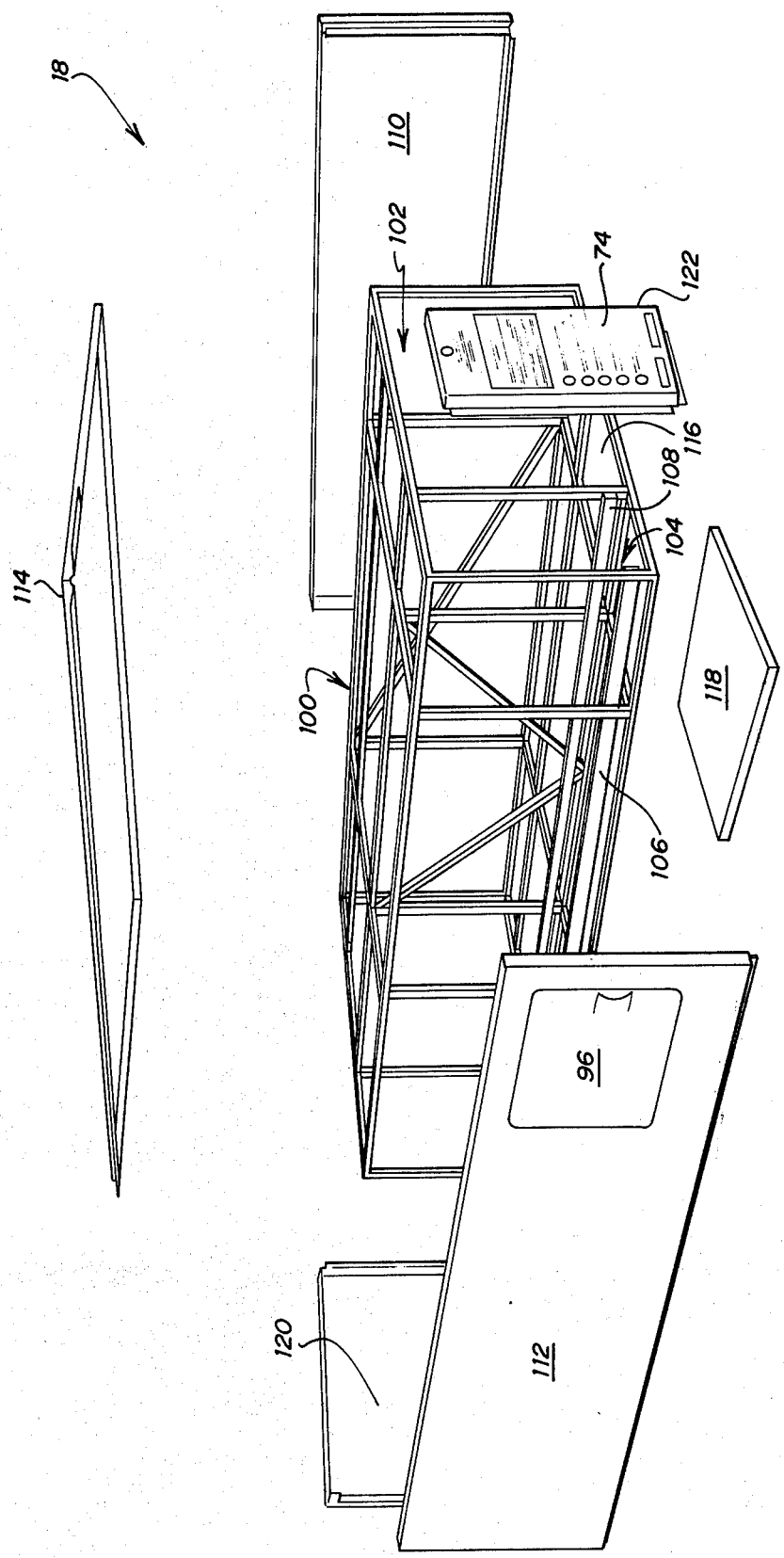

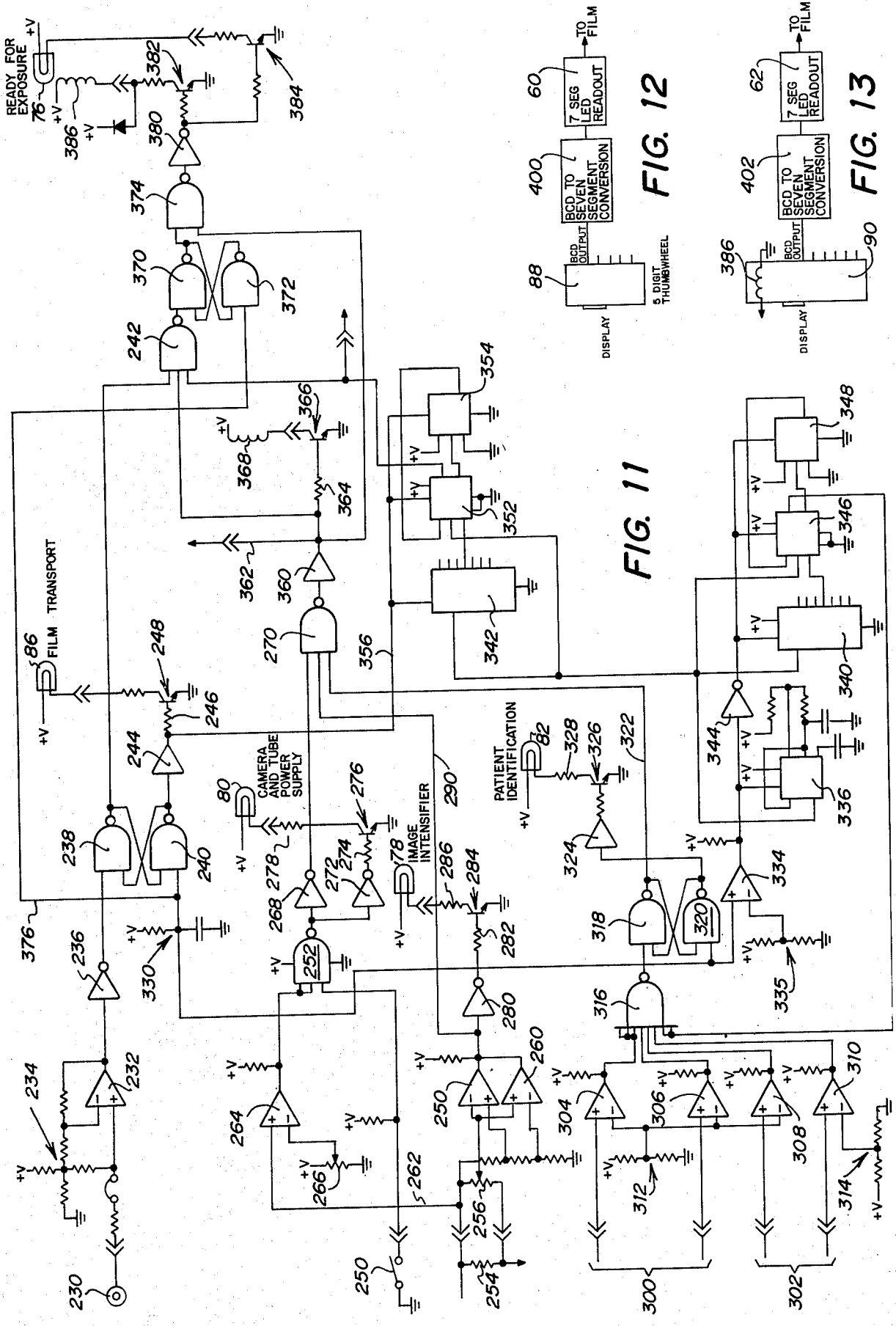

X-RAY INTENSIFICATION AND MINIFICATION SYSTEM

FIELD OF THE INVENTION

This invention relates to a radiation image recordation system, and more particularly relates to a system for intensifying and minifying representations of x-ray images.

THE PRIOR ART

Photofluorography systems have been heretofore developed for permanently recording representations of x-ray images. Such prior systems have generally included a fluorescent screen for converting x-ray images into light images, a lens system, an image intensifier and film for recording the resulting visible image. Examples of such conventional systems are described in U.S. Pat. No. 2,595,430, issued May 6, 1952, to C. M. Tuttle; U.S. Pat. No. 3,126,480, issued Mar. 24, 1964 to Bouwers and U.S. Pat. No. 3,417,242, issued Dec. 17, 1968 to R. W. Windebank.

While such previously developed systems have generally worked satisfactorily, the prior systems have been expensive due to the requirement of large and expensive objective lens systems, which were required to be radiation hardened in order to prevent deterioration as a result of exposure to the x-rays. Moreover, such previously developed systems have required excessive x-ray exposure to patients, have been of necessity quite large and have generally required that the operator move to the rear of the cabinet in order to add or remove film from the camera. Such previously developed systems have not included practical fail-safe features and have not been sufficiently mechanized for fast, efficient surveying and screening of large numbers of patients. A need has thus arisen for an economical and compact system which may be easily and simply operated to provide minified x-rays of diagnostic qualities with reasonable x-ray exposure to the patient.

SUMMARY OF THE INVENTION

The present invention provides an x-ray intensifying and minifying system which substantially reduces or eliminates problems heretofore associated with the prior art.

In accordance with the present invention, a radiation minification and recording system includes a housing with a screen in the first end thereof for being positioned to receive radiation and for converting the radiation into visible images. Reflecting surfaces are disposed in a second end of the housing for reflecting the visible images back towards the first end of the housing. An image intensifying assembly is disposed in the housing for amplifying and minifying the reflected minified images. A camera is disposed in region of the first end of the housing for recording the amplified images.

In accordance with another aspect of the invention, an intensified x-ray minification system includes a screen for converting x-rays into visible images. A first mirror is provided for reflecting the visible images along a first angled direction. A second mirror is mounted along the first angled direction for reflecting the visible images along a second angled direction such that the reflected visible images are minified and folded back parallel to the originally generated visible images. An image intensifier receives and amplifies the reflected visible images. A recording camera records the amplified reflected visible images.

In accordance with another aspect of the invention, an electric check system is provided for an x-ray intensifying and minifying apparatus wherein a camera records the output of an image intensifier tube. Circuitry generates a first signal representative of the operation of the image intensifier tube. Circuitry compares the first signal with a reference signal and generates a second signal in response to proper operation of the camera. A display is responsive to the first and second signals for indicating proper and improper operation of the apparatus.

In accordance with yet another aspect of the invention, an x-ray intensifier and minification system includes a screen for converting x-ray images into visible images. A mirror reflects the light images to an image intensifier which intensifies and minifies the reflected visible light images. A camera photographs the intensified and minified light images. Structure is provided to generate a unique number of each photograph taken by the camera. Structure is provided for generating visible light representations of the unique numbers and for directing the representations to the reflecting mirrors such that a unique number appears on each of the photographs taken by the camera.

DESCRIPTION OF THE DRAWINGS

For a more complete understanding of the present invention and for further objects and advantages thereof, reference is now made to the following description taken in conjunction with the accompanying drawings, in which:

FIG. 2 is a front perspective view of the system shown in FIG. 1;

FIG. 3 is an exploded view of the housing for the system shown in FIG. 2;

FIG. 5 is a front view of the image intensifier unit of the present system;

FIG. 6 is an end view of the camera and image intensifier unit of the invention;

FIG. 11 is a schematic diagram of the electrical system of the invention; and

FIGS. 12 and 13 are block diagrams of the register circuitry of the invention.

DESCRIPTION OF THE PREFERRED EMBODIMENT

Figure 1:
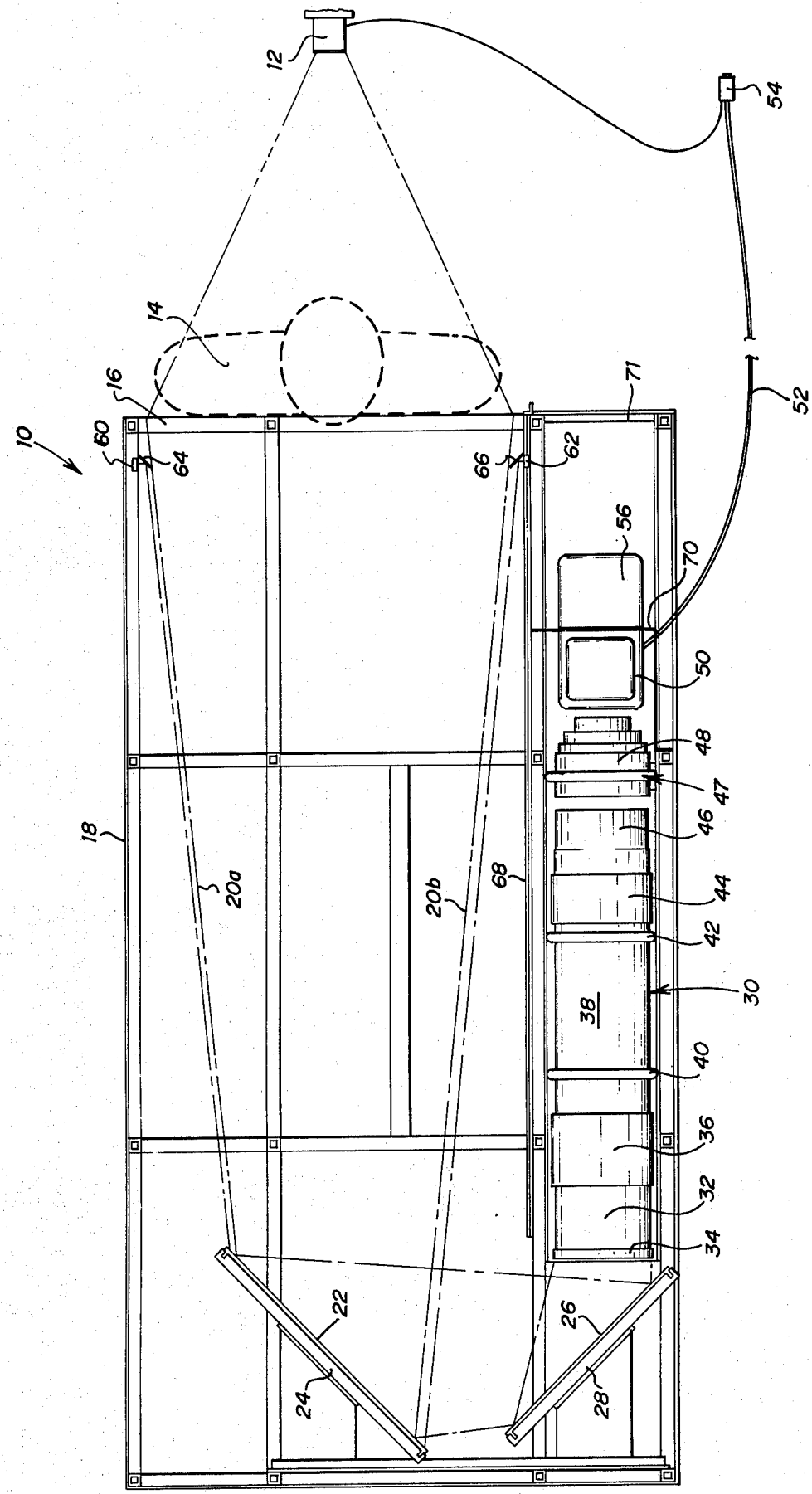
FIG. 1 is a top sectional view of the preferred embodiment of the present x-ray intensification and minification system.

FIG. 1 is a top sectional view of the present x-ray intensification and minification system generally identified by the numeral 10. A source 12 of x-ray radiation is positioned in a suitably shielded embodment to generate a beam of x-radiation which is directed into and through the object 14. Due to the x-rays passing through the subject 14, an x-ray image is formed and directed on a screen 16. Although an x-ray source 12 is illustrated in the present drawings, it will be understood that the present application is suitable for use with a variety of types of radiation to provide not only chest x-rays, but mammography, fluoroscopy and the like.

Screen 16 in the preferred embodiment comprises a bakelite cover with epoxy in order to support a thin x-ray intensifying screen. The intensifying screen includes a scintillator phosphor of rare earth oxysulfides or the like, such as the screen manufactured and sold as the Kodak Lanex Regular X-ray Intensifying Screen by Kodak Corporation. In some cases, an x-ray grid may be utilized over the screen 16 in order to allow the passage of primary radiation, but to block secondary radiation.

The x-ray images applied to the screen 16 are converted to visible light images by the scintillator phosphorous on the screen and the visible light images are directed into an elongated rectangular housing 18 along the path identified by lines 20a and 20b. The visible light image is reflected from a first mirror 22 which is mounted on a support 24 and is angled so as to reflect the visible light images at a right angle. The reflected visible light images are again reflected by a second smaller mirror 26 mounted upon a support 28. The mirror 26 is also angled in order to reflect the visible light images at approximately a 90° angle in the manner shown. Thus, the light images generated by screen 16 are "folded back" parallel to the original direction of travel of the originally generated light image.

This "folding back" eliminates the requirement of a substantial amount of shielding for the minification and intensifying assembly of the system, due to the fact that the x-ray radiation is not directly imposed upon the assembly, but only twice reflected secondary radiation is directed upon the assembly. Thus, conventional non-radiation hardended lenses may be utilized to substantially decrease the cost of the present system over previously developed systems, wherein special radiation hardened lenses were required to be utilized because of exposure to radiation.

The visible light image reflected by the second mirror 26 is directed into the minification and intensifying unit generally identified by the numeral 30. Unit 30 includes an objective lens section 32 which may comprise for example a Canon XI 90mm objective lens. A diopter corrector plate 34 is positioned over the lens 32. The resulting minified image is applied through a lens adaptor 36 to a two stage image intensifier 38. U-bolt connectors 40 and 42 support the unit 30 within the housing 18, as will be subsequently described.

As is known, the image intensifier 38 comprises a photocathode which forms an image of emitted electrons. The electrons are then electrostatically accelerated before being focused on a phosphor screen of the intensifier. The gain of the energy of the electrons is then evident as a light amplified image. The light amplified image is then passed through a lens adaptor 44 to a collimating lens 46. Lens 46 may comprise for example a Canon XI 90mm collimating lens. The resulting visual image is then applied through an imaging lens 48 held by a U-bolt 47, the lens for example comprising a Canon XI 180mm imaging lens.

The resulting amplified and minified visible image of the original x-ray image is then amplified to the lens of a camera 50 which may be operated to permanently record the representation of the original x-ray image. Camera 50 and the remainder of the system is operated through a cord 52 by a remote operation switch 54.

Switch 54 includes two positions which also control the operation of the x-ray source 12. While it will be understood that various types of cameras may be utilized, in the preferred embodiment an electric driven Hasselblad EL 500 camera with a 70mm film format and a detachable film magazine 56 is utilized. As will be subsequently described, the magazine 56 may be removed through a side door in order to allow changing of the film without removing the camera. The motor drive 57 for the camera is mounted beneath the camera 50 and the film magazine 56.

An important feature of the present device are light emitting diode (LED) displays 60 and 62 which generate visible representations of number sequences. The number sequences generated by the LEDs are reflected from mirrors 64 and 66 and off the mirrors 22 and 26 to the unit 30 and subsequently to the camera 50. In this manner, unique number representations may be imposed upon the image of the pictures taken by the camera 50 in order to allow unique designation of each picture taken by the camera. Due to the mirrors 64 and 66, LEDs 60 and 62 and their associated logic circuitry are shielded from exposure to direct x-ray radiation. LED 60, as will be subsequently described, is utilized to provide an automatically incremented number according to a set numbering scheme for each different film frame. LED 62 generates a number which may be set by a thumbwheel switch 88 to be subsequently described, on the front panel of the housing 18 by the person operating the x-ray machine.

A lead shield 68 is formed along one side of the unit 30 and the camera 50 in order to prevent exposure to direct x-rays. Similarly, a lead shield portion 71 is disposed behind the camera 50 for protection from the direct x-ray exposure. Due to the double folding reflecting arrangement of the present system, only two lead shields 68 and 71 are required, thereby eliminating the requirement of extensive shielding with attendant weight and cost problems. A light baffle 70 is formed around the camera 50 to protect the film in the camera from light leaks through door 96.

FIG. 2 is a perspective view of system 10 illustrating the compact size of the system. In the preferred embodiment, the housing 18 is provided with dimensions of 17 inches × 25 inches × 40 inches, with a total weight of 100 pounds. The present system thus occupies a relatively small space and is easly portable, yet provides diagnostic quality x-rays in an easy to operate manner. The screen 16 has a viewing field dimensions of 14 by 16 inches and may be positioned adjacent the chest or other area of the patient to be x-rayed.

An important aspect of the invention is the panel 74 which includes a ready for exposure light 76 which is not illuminated until all components of the system have been electronically checked just prior to operation of the x-ray source 12. In this way, the patient is not exposed to x-ray radiation unless the system is functioning properly.

Panel 74 also includes an image intensifier light 78 which is illuminated if the current being applied to the image intensifier is above or below a predetermined level. A camera and tube power supply light 80 is illuminated if the voltage applied from the power supply to the intensifier tube is below a predetermined level, or if the magazine 56 is not in place. A patient identification lamp 82 is illuminated if one of the LEDs 60 and 62 has a burned out segment. An automatic exposure control lamp 84 is illuminated when the x-ray intensity reaches an excessive level, as sensed by a sensor in the system. A film transport lamp 86 is illuminated when the film transport or shutter of the camera 50 has not operated according to the prescribed sequence. The lamps 78–86 are thus illuminated only if a malfunction occurs in the system. If a malfunction occurs, the light 76 will not be illuminated and x-rays are not applied to the patient thereby illuminating irradiation of the patient if a proper picture is not able to be taken.

A register 88 comprises five digit manually operated thumbwheel register in which any desired sequence of five digits may be manually dialed. The operator of the device may use the thumbwheel register 88 to dial in a patient number or code corresponding to the particular patient being x-rayed. As will be subsequently described, this sequence of five digits is displayed by the LED 60 and reflected to the camera 50. A six digit register 90 is automatically incremented each time a picture is taken by the camera 50. The digits contained within the register are displayed by LED 62 and reflected to the camera 50. Thus, each picture taken by the camera 50 includes a visual representation of the settings of the registers 88 and 90.

An opening 94 is formed in the side of the housing 18 and a door 96 is pivotally connected by hinge 98. Normally, the door 96 is shut during operation of the system. When it is desired to change the film in the camera, the door 96 is opened and the film magazine 56 interchanged with a fresh magazine. Thus, the entire camera need not be removed, thereby maintaining the present focus of the camera at all times.

FIG. 3 is an exploded diagram illustrating the construction of the housing 18. A rigid framework 100 comprises meta legs welded in a lattice-like rectangular configuration. The framework includes a first unobstructed area 102 wherein the light images generated by the screen 16 are directed toward the rear mounted mirrors. A second area 104 having a narrower width than the area 102 is formed to accommodate the minification and intensification system. An important aspect of the invention is the provision of rails 106 and 108 which slidably support a frame carrying the minification and intensification unit 30 and camera 50, such that the unit 30 and camera 50 may be slid outwardly for maintenance or replacement.

Side walls 110 and 112 are adapted to be affixed to the framework 100 by screws and the like. A top metal rectangular piece 114 fits over the top of the housing. A rectangular bottom piece 116 is illustrated in place on the bottom of the framework 100. A mounting plate 118 is adapted to be affixed to the bottom of the plate 116 to enable mounting of the unit on a suitable stand, tripod or the like. A rear plate 120 is adapted to be affixed to the rear of the framework 100, while a plate 122 is adapted to be affixed to the front of the framework to cover the area 104. Plate 122 may be removed from removal of unit 30 and camera 50. The panel 74 previously described is affixed on the front plate 122. The present housing is constructed in a light tight configuration and is extremely rigid and essentially maintenance free.

Figure 4:
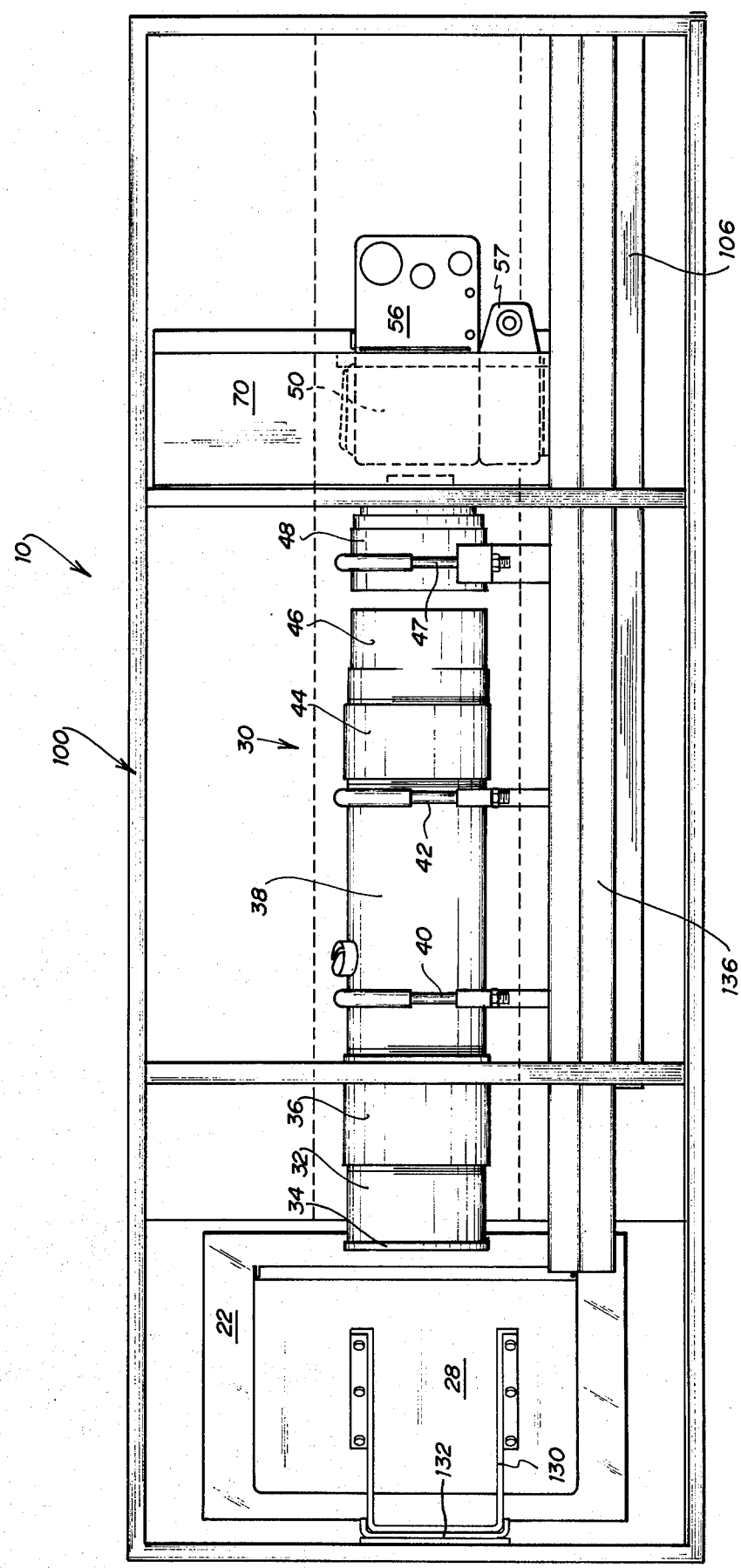
FIG. 4 is a sectional side view of the housing shown in FIGS. 1 and 2.

FIG. 4 also illustrates a U mounting bracket 130 which is connected at 132 to the rear of framework 100 and is bolted at the opposite end to mirror support 28 which supports the second mirror 26. FIG. 4 also shows a portion of the first mirror 22, which may be seen to be larger than second mirror 26. The second mirror 26 reflects the visible light images into the objective lens 32 and through the lens adaptor 36 to the light intensifier unit 38. FIG. 4 illustrates how the U-bolts 40, 42 and 47 are rigidly bolted to the frame slidable along rails 106 and 108.

The output of the image intensifier unit 38 is applied through the lens adaptor 4 and through the collimating lens 46 and the imaging lens 48 to the camera 50. As previously noted, the magazine 56 may be detached from the camera 50 to enable the easy changing of film. A light baffle 70 fits over and around the camera 50 to provide light baffling for the camera.

FIG. 5 is a front view of the minification and intensification unit 30. The U-bolt 40 fits over the top portion of the image intensifier 38 and is fastened to a yoke 140 by bolts 142 and 144. Yoke 140 rests on tracks 146 and 148 which are rigidly mounted to a U shaped frame 150. The second U shaped frame 152 is bolted to frame 150 to form the track 136. The yoke 140 is bolted to the track 136 by bolts 154.

FIG. 6 is a rear view of the camera magazine 56 and the camera motor drive 57. As is shown, the U-bolt 47 is connected to a yoke 158 by bolts 160 and 162. The motor drive 57 is connected to a mounting fixture 164 by a bolt 166. Mounting fixture 164 is slidable along the track 146 and 148 to the desired position, whereupon it is rigidly attached to the track 136.

Figure 7:
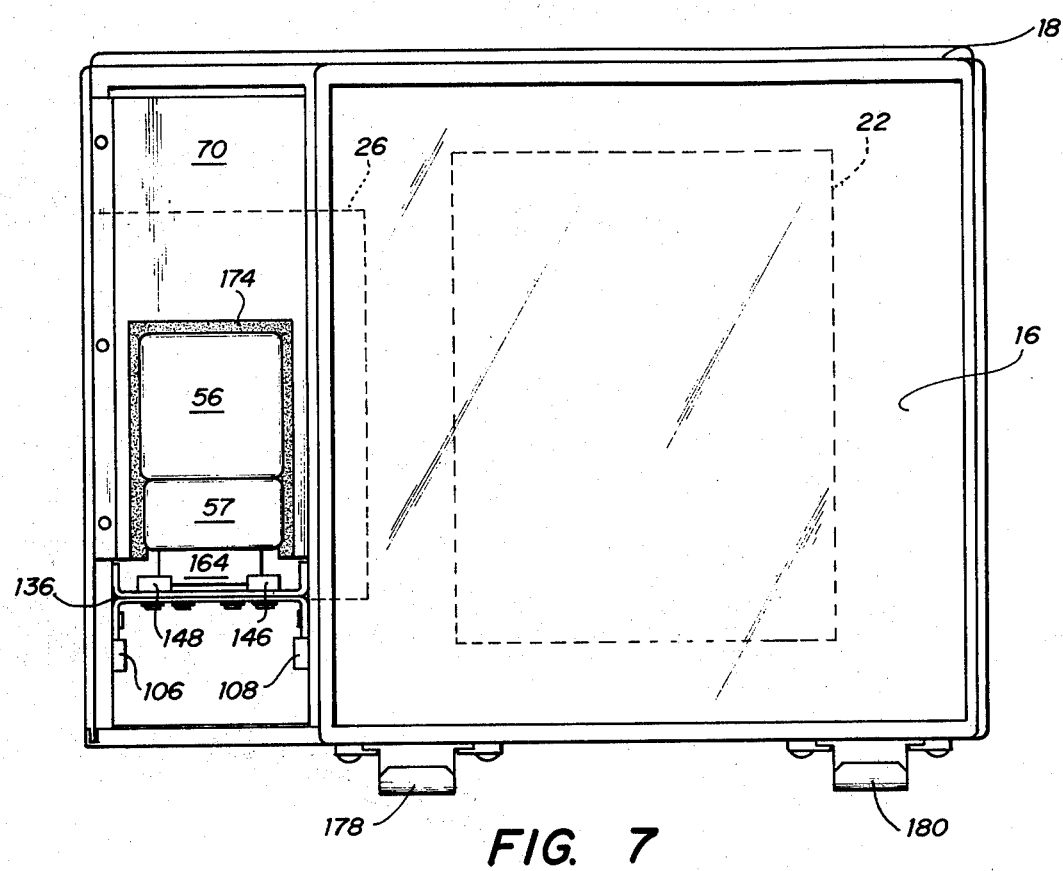
FIG. 7 is a front view of the present housing.

FIG. 7 is a front view of housing 18, with the front panel 74 removed to illustrate the film magazine 56 and camera motor drive 57. The track 136 is supported on rails 106 and 108 in order to be slid outwardly from the housing 18 for maintenance and adjustment. FIG. 7 also illustrates the baffle 70 which includes U shaped cutout 174 for fitting over the camera 50 to prevent light from exposing film within the camera. FIG. 7 illustrates the positioning of the mirror 22 and the mirror 26. Grid holders 178 and 180 are mounted below the housing 18 and are slidable between retracted and extended positions. In the extended position, an x-ray grid may be placed on holders 178 and 180 to extend over the screen 16.

Figure 8:
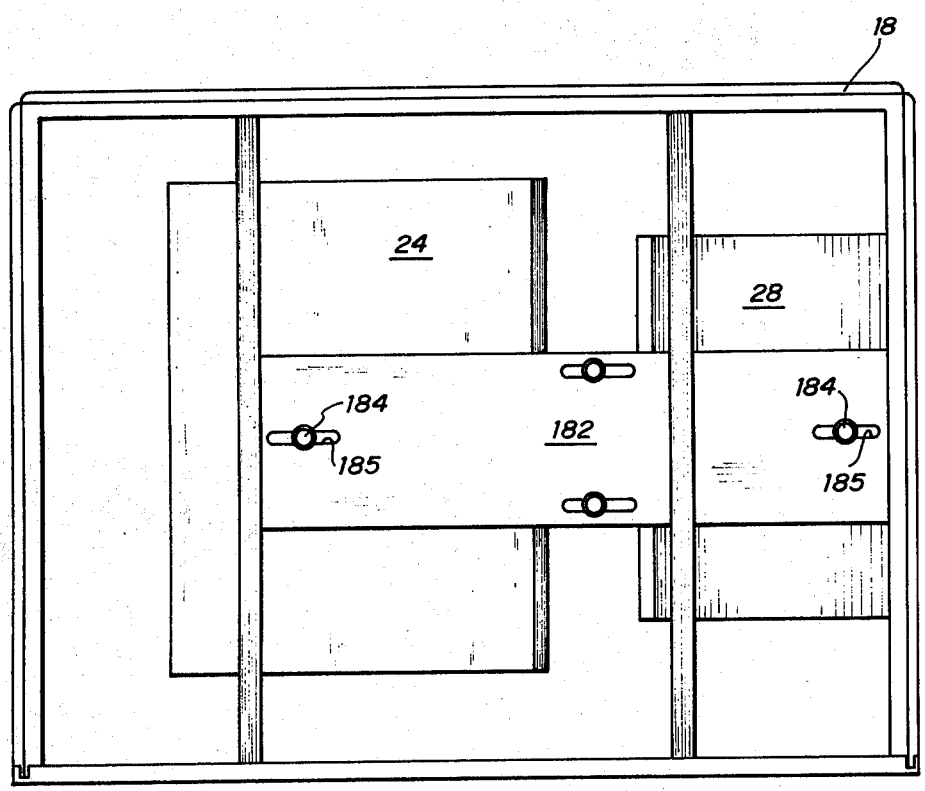
FIG. 8 is an end view, with the rear panels removed, of the present system.

FIG. 8 is a rear view of the housing 18 with the rear plate 120 removed, illustrating a mounting frame 182 which is rigidly attached at the rear to the framework 100. The U mounting bracket 130 which holds the mirror supports is mounted to frame 182 by bolts 184. Apertures 185 are formed in the frame 182 to enable adjustment of the position of mirrors.

Figure 9:
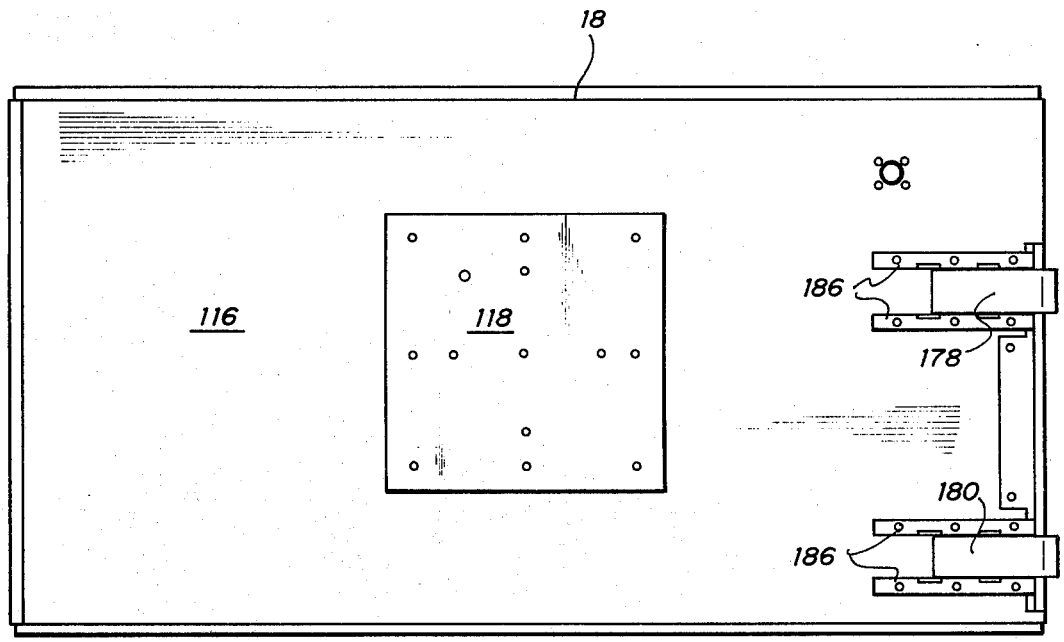
FIG. 9 is a bottom view of the present housing.

FIG. 9 is a bottom view of housing 18 which shows plate 118, previously described, affixed to the bottom 116 to enable attachment of the housing 18 to the suitable mounting platform. The grid support holders 178 and 180 are movable along tracks 186 for being moved into the retracted or extended position for holding the x-ray grid previously described.

Figure 10:
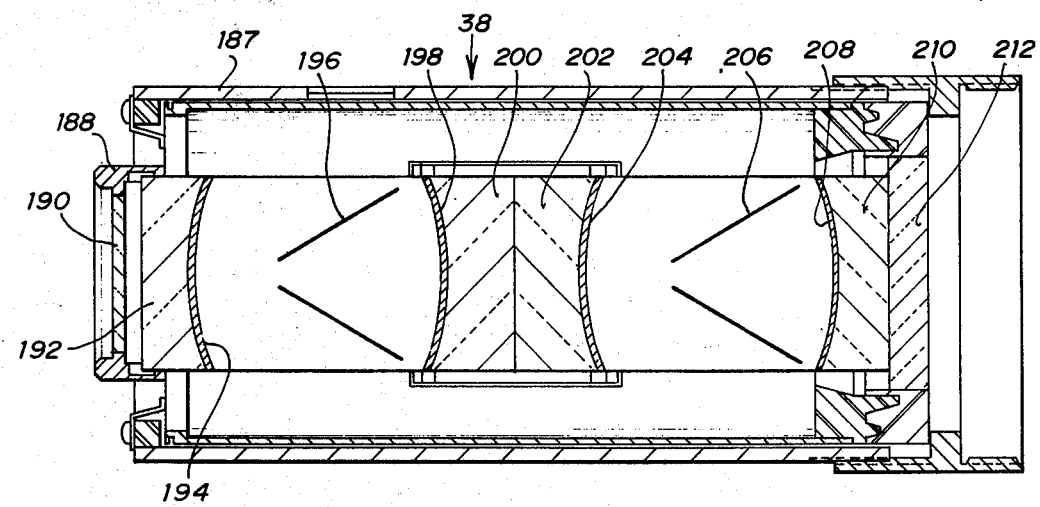
FIG. 10 is a sectional view of the image intensifier used with the present invention.

FIG. 10 is a sectional view of the image intensifier 38. The intensifier includes a cylindrical housing 187 having a plastic holder 188 mounted in one end. A glass window 190 is mounted in the holder 188 to transmit visual images through a fiber optics assembly 192 to a photocathode 194. The photocathode converts the visible light into electrons which are directed through electron lens 196 in order to be accelerated and focused on a P-20 phosphor layer 198. The phosphor layer converts the electrons into photons to provide visible light which is applied through a fiber optic assembly 200 which is mated with a fiber optic assembly 202. Fiber optics 202 directs visible light to a second image intensifier stage which includes a photocathode 204, electron lens 206, phosphor layer 208 and fiber optics 210. The resulting intensified and minified image is applied through a glass window 212 to the collimating lens 46 in the manner previously described.

The use of the two stage image intensifier is an important aspect of the present invention, as a gain of 1600 foot lamberts per foot candle is provided. In prior art systems, a single stage image intensifier has been utilized which requires a much larger photocathode and larger objective lens, thereby requiring expensive objective lens and large cabinets. The present two stage image intensifier provides a 40mm diameter input and output system to provide the desired resolution for the system without the requirement of expensive lens systems. A suitable image lens intensifier for use with the present invention may comprise for example a two stage image intensifier utilizing the intensifiers in the Varo Models 8605 and 8606 Image Intensifier Assemblies manufactured and sold by The Electron Devices Division of Varo Corporation.

FIG. 11 is an electrical schematic of the circuitry interconnecting the hand-held switch 54 and the lights on panel 74 and the control circuitry for the device. Referring to the drawing, a microphone 230 is disposed adjacent the camera 50 in order to detect the sound of operation of the shutter of the camera. The microphone is connected to the positive input of a comparator 232. The negative input of the comparator 232 is connected to a resistance network 234 in order to provide a reference voltage to the comparator. The output of the comparator is applied through an inverter 236 to the input of a NAND gate 238. Gate 238 is connected in a latch configuration with a NAND gate 240. The Q output of the latches is connected to the input of a NAND gate 242. The Q output of the latch is applied through an amplifier 244 and a resistor 246 to the base of a transistor 248. The collector of the transistor 248 is connected to the film transport light 86 which is mounted on front panel 74.

A normally closed microswitch 250 is disposed adjacent the film magazine 56 in housing 18 and is maintained closed as long as the film magazine is in place. When the film magazine 56 is removed, the switch 250 is opened. Switch 250 is connected to an input of a NAND gate 252. A sensing resistor 254 is connected in series with the image intensifier tube 38 and the power supply to the tube. A variable resistance 256 is connected across resistor 254 and applies an indication of the current being applied to the intensifier tube to inputs of comparator 258 and 260. Voltage is applied via lead 262 to the positive input of a comparator 264. A reference voltage is applied from a variable resistance 266 to the negative input of the comparator 264. The output of comparator 264 is applied to the second input of the NAND gate 252. The output of gate 252 is applied through an inverter 268 to an input of a NAND gate 270. The output of gate 252 is also applied through an amplifier 272 and a resistance 274 to the base of a transistor 276. A collector of transistor 276 is applied via a resistor 278 to the camera and tube power supply lamp 80 which is mounted on front panel 74.

The outputs of comparators 258 and 260 are applied through an inverter 280 and resistor 282 to the base of a transistor 284. The collector of transistor 284 is connected through a resistance 286 to the image intensifier light 78 mounted on panel 74. The outputs of the comparators 258 and 260 are also applied via a lead 290 to an input of NAND gate 270.

Terminals 300 are connected to sense resistors, not shown, for sensing the voltage applied to LED 60 (FIG. 1). Terminals 302 are connected to sense resistors, not shown, which are connected to sense the voltage applied to LED's 62 (FIG. 1). The output of terminals 300 and 302 are applied to comparators 304, 306, 308 and 310, respectively. Reference voltage is applied to comparators 304, 306 and 308 from a resistive network 312. Reference voltage is applied to comparator 310 from a resistance network 314. The outputs of the comparators 304-310 are applied to a multi-input NAND gate 316. The output of the NAND gate 316 is applied to a NAND gate 318 connected in a latch configuration with a NAND gate 320. The Q output of the latch is applied via lead 322 to the input of a NAND gate 270. The $\overline{Q}$ output of the latch is applied through an amplifier 324 to the base of a transistor 326. The collector of transistor 326 is connected through a resistor 328 to the patient identification lamp 82 previously shown as being mounted on panel 74.

A reference voltage is developed across a capacitive and resistive network 330 and is applied via lead 332 to an input of NAND gate 320 and as an input to a comparator 334. A reference voltage is applied from a resistive network 335 to the negative input of a comparator 334. The output of comparator 334 is applied to a timer interconnected as a square wave oscillator 336. The output from the oscillator 336 is applied to clock a seven segment binary counter 340 and a second seven segment binary counter 342. The output of comparator 334 is also applied through an invertor 344 to interconnected flip-flops 346 and 348. The Q1 output of flip-flop 346 is applied via lead 350 to serve as an enabling input to a NAND gate 316. The oscillator 336, counter 340 and flip-flops 346 and 348 operate as a delay to allow the LEDs to warm up prior to testing.

The counter 342 is interconnected with flip-flops 352 and 354. The output of amplifier 244 is also applied via lead 356 to the counter 342 and to the flip-flops 352 and 354. The Q1 output of the flip-flop 352 is applied as a blanking signal to control the BCD to seven segment converters for operating the LEDs to be subsequently described in FIGS. 12 and 13.

The output of NAND gate 270 is applied through an inverter 360 to generate a signal via lead 362 which is applied to the lamp test terminals of the BCD to seven segment converters as shown in FIGS. 12 and 13. The output of inverter 360 is also applied to an input of the NAND gate 242 and through a resistor 364 to the base of a transistor 366. The collector of transistor 366 is connected to control the camera shutter relay 368 in order to control the opening and closing of the camera shutter in the manner to be subsequently described.

The Q1 output of flip-flop 352 is also applied as an input to NAND gate 242. The output of gate 242 is applied to a NAND gate 370 which is interconnected in a latch configuration with a NAND gate 372. the output of the latch is connected to a NAND gate 374. The output of the capacitive and resistive network 330 is applied via a lead 376 to the input of a NAND gate 372. The output of gate 374 is applied through an inverter 380 to the base of a transistor 382. The output of inverter 380 is also applied to the base of a transistor 384. The collector of transistor 382 is connected to a counter relay coil 386 which controls the advance of the register 90 previously shown in FIG. 2. The collector of transistor 384 is connected to the lamp 76 mounted on panel 74 previously described with respect to FIG. 2.

In operation of the electrical circuitry shown in FIG. 11, the operator places the patient at the desired position in front of the screen 16. The operator then depresses the hand-held switch 54 (FIG. 2) to the first switch position. This operation of switch 54 turns the x-ray tube on and causes the anode of the x-ray tube to rotate in the known manner, in order to evenly distribute the electron beam over the anode in order to prevent x-ray tube damage. During the one to two second interval required for the anode to reach required speed, the interrogation of the present system is accomplished.

When the anode starts to rotate upon the first depression of the switch 54, bias voltage is applied to all bias points on the circuitry shown in FIG. 11 and the present system begins operation. Upon receiving bias voltage, all of the latches and switches of the system are reset to the desired position.

At this point, the LED's 60 and 62 are tested to insure that all segments of the LEDs are working properly. Power is applied via lead 362 to the LT terminals of the converters of the LED circuits, shown in FIGS. 12 and 13, in order to light all segments of all of the LEDs 60 and 62. The current passing through the LEDs is then sensed by sensing resisters and applied to terminals 300 and 302. These current levels are compared with the levels generated by resistive networks 312 and 314 by comparators 304-310. If all of the LED segments are operating satisfactorily, suitable inputs are applied to the NAND gates 316. The time of testing of the LED is determined by operation of the oscillator 336, counter 340 and flip-flops 346 and 348 which provide a time delay in order to enable the LEDs 60 and 62 to properly warm up.

When sufficient time has been allowed for the LEDs to warm up, an enabling signal is applied via lead 350 to the gate 316. At this time, if all of the LED segments are operating satisfactorily, the level from gate 316 is detected by a latch comprising gates 318 and 320. The latch is set by the level of the gate 316.

If the LED test is satisfactory, an enabling signal is applied via lead 322 to one of the inputs of gate 270. If the LED test is unsatisfactory, because one of the LED segments has burned out or the like, the proper logic signal is not output at gate 316 and the latch is not set. The resulting output from the latch gate 320 is amplified by amplifier 324 and applied to the base of transistor 326. This causes the lamp 82 to be lit to indicate on the panel 74 that the patient identification system has a malfunction. If this occurs, x-rays will not be applied to the patient by the operator. After the time period determined by the oscillator 336 counter 340 and flip-flops 346 and 348, the LEDs 60 and 62 are then turned off and the LED testing is complete.

Also after the power has been applied to the circuit, the camera and the tube power supply are checked. Switch 250 detects whether or not the film magazine 56 is properly in place. If so, an enabling system is applied to NAND gate 252. In addition, the tube power supply is detected by the sensing resistor 254 and the power supply voltage is compared with a reference voltage by comparator 264. If the power supply voltage is satisfactory, an enabling signal is applied to gate 252. If the proper input signals are sensed by gate 252, an enabling signal is applied through inverter 268 to the input of NAND gate 270. If a malfunction is detected by the switch 250 or by the comparator 264, a logic level is applied via amplifier 272 to the base of transistor 276 and the lamp 80 is lit to indicate that a malfunction exists either in the camera or in the tube power supply and x-rays will not be applied to the patient.

Testing is also accomplished from the output of the sensing resistor 254 of the current applied to the image intensifier 38. The current level is sensed by comparators 258 and 260 and compared with preset high and low levels. If the current is excessively low or high, an indication is provided through inverter 280 to render the transistor 284 conductive in order to illuminate the image intensifier lamp 74 to indicate that a malfunction has occurred in the current of the image intensifier, so that x-rays will not be applied to the patient. If the image intensifier current is satisfactory, an indication is applied via lead 290 to the input of NAND gate 270.

If all of the aforedescribed functions test out properly, three enabling logic levels will be simultaneously applied to the input of NAND gate 270 and a logic level will appear at the output of gate 270 in order to energize transistor 366 to energize the camera shutter relay 368 to open the camera shutter. If the camera shutter opens properly, a noise will be generated by the camera which is picked up by microphone 230. This noise is compared with a predetermined reference level by comparator 232. If the proper signal level is generated the latch comprised of gates 238 and 240 will be set and will generate an output from the Q terminal to the input of a NAND gate 242. If the predetermined noise of operation of the camera shutter is not detected, the light renders the transistor 248 conductive in order to illuminate the lamp 86 on the panel 74 (FIG. 2) to indicate that the film transport is malfunctioning.

If the camera shutter opens properly and the predetermined noise is detected, blanking of the LEDs is overcome after a suitable time interval determined by the counter 342 and flip-flops 352 and 354, and the LEDs are illuminated in accordance with the number sequences stored in registers 88 and 90 (FIG. 2). The number sequences are reflected from the mirrors 64 and 66 (FIG. 1) and are reflected from mirrors 22 and 26 through the open shutter to expose the film with the suitable patient identification number. These numbers are applied for approximately 200 millisecond intervals to expose the film. After the LEDs are turned on, the gate 242 sets the latch comprising gates 370 and 372 and a predetermined level is applied to gate 374. If all systems have operated properly as of this point, a suitable logic signal is generated from gate 374 and is applied to energize transistors 382 and 384. The counter relay coil 386 is then energized in order to increment the register 90 for one count to properly identify the next picture to be taken. In addition, the ready-for-exposure lamp 76 on panel 74 is illuminated to indicate to the operator that all systems are operating properly.

Within a predetermined time, such as 10 seconds after the lamp 76 becomes illuminated, the operator moves the switch 54 to a second position in order to turn on the x-ray tube 12 to expose the patient to radiation in order to generate the x-ray images to be recorded on the camera 50. After a suitable time interval of exposure, the switch 54 is released and radiation to the patient is terminated. The film is automatically cycled one cycle and all power is terminated from the circuit and all the gates of the circuit are reset. If the lamp 76 is not illuminated prior to exposing the patient to x-ray, the operator knows that a malfunction has occurred and the patient is not unnecesarily subjected to radiation.

FIG. 12 illustrates the electronic circuitry for control of the LED 60 (FIG. 1). The register 88 comprises a conventional 5-digit thumbwheel switch which may be manually set in any desired combination of five digits by the operator. When set, the thumbwheel switch register generates the binary coded output representative of the five digits set therein. Each of the five BCD outputs is applied to a BCD to seven segment converter 400 which may comprise for example a CD 4511 AE converter. The output of the converter controls a seven segment LED readout 60 which generates one of the digits applied to the camera 50. It will be understood that five converters 400 are provided to control five LEDs 60.

FIG. 13 is similar to that shown in FIG. 12, with the exception that a six digit register 90 is automatically incremented by operation of the counter relay coil 386. The output of the register 90 is a binary coded output which is applied to six BCD to seven segment converters 402. The output of each converter controls a seven segment LED readout 62.

It will thus be seen that the present invention provides a unique practical x-ray recording system which may be advantageously utilized to screen large number of patients and to provide minified x-ray records of diagnostic quality. The present system includes automatic self-checking circuitry to eliminate unnecessary radiation of a patient upon malfunction of the system. The present system does not require expensive large optics or radiation hardened optics, yet provides excellent minified x-rays which may be easily attached to a patient's folder.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. A radiation minification and recording system comprising:
   a housing,
   a screen in a first end of said housing for being positioned to receive radiation and for converting the radiation into visible images,
   reflecting surfaces disposed in a second end of said housing for reflecting said visible images toward said first end of said housing,
   image intensifying means disposed in said housing for intensifying and minifying the reflected images, and
   recording means disposed in the region of said first end of said housing for recording the amplified minified images.

2. The radiation minification and recording system of claim 1 wherein said visible images are reflected back along a line perpendicular to said screen.

3. The radiation minification and recording system of claim 1 wherein said reflecting surfaces comprise:
   a first mirror for reflecting said visible images for a first right angle, and
   a second mirror for reflecting said visible images for a second right angle back toward said first end of said housing.

4. The radiation minification and recording system of claim 3 wherein said first mirror is larger than said second mirror.

5. The radiation minification and recording system of claim 1 wherein said image intensifying means includes optical lenses and means for shielding said optical lenses from primary and secondary radiation.

6. The radiation minification and recording system of claim 1 and further comprising:
   means for generating visible indicia and for directing said indicia to said recording means for recording in association with said reflected images.

7. The radiation minification and recording system of claim 1 wherein said recording means comprises a camera rigidly mounted in said housing and having a film magazine operable to be removed from said housing.

8. An intensified x-ray minification system comprising:
   screen means for converting x-rays into visible images,
   a first mirror for reflecting said visible images along a first angled direction,
   a second mirror mounted along said first angled direction for reflecting said visible images along a second angled direction, such that the reflected visible images are minified and folded back along one side of the originally generated visible images,
   image intensifying means for receiving and amplifying reflected visible images, and
   means for recording the amplified reflected visible images.

9. The x-ray minification system of claim 8 wherein said first and second angled directions are normal to one another.

10. The x-ray minification system of claim 8 wherein said first mirror is larger than said second mirror.

11. The x-ray minification system of claim 8 wherein said reflected images are directed parallel to said visible images.

12. The x-ray minification system of claim 8 wherein said recording means is disposed adjacent the side of said screen means.

13. An intensified x-ray minification system comprising:
   a housing having opposed front and rear ends,
   a phosphor screen disposed in said front end of said housing for receiving x-ray images of an object irradiated by x-rays and for generating light images corresponding to said x-ray images,
   a mirror system mounted within said housing adjacent said rear end for reflecting said light images toward said front end of said housing,
   an image intensifying assembly for amplifying and minifying said reflected light images,
   a camera located in the region of said front end of said housing for recording said amplified and minified light images, said camera being shielded from said x-rays.

14. The x-ray minification system of claim 13 wherein said mirror system comprises:
   a first mirror mounted in one rear corner region and a second mirror mounted in a second rear corner region of said housing.

15. The x-ray minification system of claim 13 wherein said housing is rectangular with a length greater than the width and height.

16. The x-ray minification system of claim 13 and further comprising:
a control panel mounted on said front end of said housing adjacent said screen.

17. The x-ray minification system of claim 16 wherein said control panel includes indicia for indicating proper operation of predetermined elements of said system, and
means connected to said indicia for determining proper operation of said elements.

18. The x-ray minification system of Claim 17 wherein said means for determining proper operation comprises:
means for detecting sounds located adjacent said camera, and
circuitry responsive to said detecting means for comparing the sounds of said camera against a predetermined standard.

19. The x-ray minification system of Claim 13 and further comprising:
a frame having said image intensifying assembly and said camera mounted thereon,
rail means mounted within said housing along one side thereof for slidably receiving said frame, and
a panel detachably mounted on the front of said housing to enable removal of said rail means.

20. The x-ray minification system of claim 13 wherein said camera includes a film magazine,
a door disposed in the side of said housing adjacent said camera to allow withdrawal of said film magazine.

21. The x-ray minification system of Claim 13 wherein said image intensifying assembly includes two back-to-back image intensifiers.

22. The x-ray minification system of claim 13 wherein said image intensifying assembly includes optical lens and means for shielding said optical lens from primary and secondary radiation.

23. The x-ray minification system of claim 13 and further comprising:
means for generating visible indicia images, and
means for reflecting said visible indicia images to said camera for recording.

24. The x-ray minification system of claim 23 and further comprising:
register means mounted on the front of said housing for indicating said visible indicia images to the operator.

25. The x-ray minification system of claim 24 and further comprising:
first register means settable to a desired value by the operator, and
a second register automatically set in accordance with operation of said camera.

26. The x-ray minification system of claim 24 wherein said means for generating comprise light emitting means responsive to the setting of said register means, and
mirror means for reflecting said visible indicia images toward said mirror system.

27. In an x-ray intensifier and minification system, the combination comprising:
means for converting x-ray images into visible light images,
means for reflecting said light images,
means for intensifying and minifying said reflected visible light images,
a camera for photographing the intensified and minified light images,
means for generating a unique number for each photograph taken by said camera,
means for generating visible light representations of said unique numbers and for directing said representations to said reflecting means such that a unique number appears on each of the photographs taken by said camera, said means for generating visible light representations including a first register manually settable to any of a plurality of numbers and a second register, and
means for automatically setting said second register in response to detection of sounds of operation of said camera.

28. The combination of claim 27 wherein said means for generating visible light comprises light emitting devices for emitting visible digits.

29. The combination of claim 27 and further comprising:
means for checking the operation of said means for generating visible light representations prior to generation of said representations of said unique numbers.

30. An electronic check system for an x-ray intensifying and minifying apparatus wherein a camera records the output of an image intensifier tube comprising:
means for sensing an electrical signal representative of the operation of said image intensifier tube and for generating a first signal representative of the operation of said image intensifier tube,
means for comparing said first signal with a reference signal,
means for generating a second signal in response to proper operation of said camera, and
display means responsive to said first and second signals for indicating proper and improper operation of said apparatus.

31. The electronic check system of claim 30 wherein said means for generating a second signal comprises:
means for detecting the proper location of the film magazine of said camera.

32. The electronic check system of claim 30 wherein said means for generating a second signal comprises:
means for detecting the sound of proper operation of said camera shutter.

33. The electronic check system of Claim 30 and further comprising:
means responsive to said first and second signals for generating visible light representations of a unique number sequence corresponding to the picture being taken by the camera,
means for energizing said means for generating visible light representations,
means for checking proper operation of said means for generating visible light representations during said energization, and
means for preventing energization of said display means upon detection of improper operation of said means for generating.

34. The method of recording an x-ray image with an image intensifier and a camera comprising:
automatically interrogating predetermined operating characteristics of said intensifier and said camera,
comparing said interrogated characteristics with preset standards to detect malfunctions,
generating x-rays only if no malfunctions are detected, converting said x-rays to visible images, directing said visible images through said image intensifier, and recording the output of said image intensifier with said camera.

35. The method of Claim 34 wherein said step of interrogating comprises:

detecting the sounds of operation of said camera.

36. The method of claim 34 wherein said step of interrogating comprises:

detecting the voltage level of predetermined portions of said intensifier.

37. The method of claim 34 wherein said step of interrogating comprises:

detecting the proper position of the film magazine for said camera.

38. The method of Claim 34 and further comprising:

generating light images of predetermined number sequences for recording on said camera, and checking proper operation of the light generator prior to generation of said x-rays.

39. In an x-ray intensifier and minification system, the combination comprising:

means for converting x-ray images into visible light images, means for reflecting said light images, means for intensifying and minifying said reflected visible light images, a camera for photographing the intensified and minified light images, means for generating a unique number for each photograph taken by said camera, and means for generating pulsed visible light representations of said unique numbers and for directing said representations to said reflecting means for a predetermined time interval prior to generation of said minified light images, such that a unique number appears on each of the photographs taken by said camera.

* * * * *

UNITED STATES PATENT AND TRADEMARK OFFICE
CERTIFICATE OF CORRECTION

PATENT NO. : 4,015,126

DATED : March 29, 1977

INVENTOR(S) : James R. Herrington

It is certified that error appears in the above-identified patent and that said Letters Patent are hereby corrected as shown below:

Col. 6, line 6, "lens adapter 4" should be --lens adapter 44--.

Col. 8, line 58, "372.the output" should be --372. The output--.

Signed and Sealed this

Fourth Day of October 1977

[SEAL]

Attest:

RUTH C. MASON
Attesting Officer

LUTRELLE F. PARKER
Acting Commissioner of Patents and Trademarks